United States Patent [19]

Pilling

[11] Patent Number: 5,402,771

[45] Date of Patent: Apr. 4, 1995

[54] ANTERIOR COMMISSURE LARYNGOSCOPE

[75] Inventor: William H. Pilling, North Wales, Pa.

[73] Assignee: Pilling Co., Fort Washington, Pa.

[21] Appl. No.: 736,410

[22] Filed: Jul. 26, 1991

[51] Int. Cl.⁶ .............................................. A61B 1/267
[52] U.S. Cl. ........................................ 128/10; 128/11
[58] Field of Search ....................... 128/10, 11, 15, 16, 128/3

[56] References Cited

U.S. PATENT DOCUMENTS 3,884,222  5/1975  Moore ............................... 433/31 X
3,943,920  3/1976  Kandel .................................. 128/11

FOREIGN PATENT DOCUMENTS 612116 11/1948 United Kingdom ................... 128/11

OTHER PUBLICATIONS

Woodrow, "Improved Suspension Larynogoscope For Use With Operative Microscope", 1970, p. 412.

Pilling Catalog, Pilling Endoscopic Instruments, 1986 pp. 14, 18 and 20.

Primary Examiner—Richard J. Apley
Assistant Examiner—Donna L. Maraglio
Attorney, Agent, or Firm—Howson & Howson

[57] ABSTRACT

A laryngoscope, for use with a binocular operating microscope, has a tube with a flared distal end and a narrow intermediate portion allowing manipulation of the tube. The proximal end of the tube is flared horizontally to an extent such that the centerlines of both objective lenses of the microscope enter the proximal opening of the tube even when the microscope is moved to the left and right to view portions of the larynx spaced laterally from the central axis of the tube. When the microscope is moved laterally, the centerline of one of the lenses intersects the interior wall of the tube, which is dark. Therefore the annoying effect of seeing objects external to the laryngoscope tube with one eye is avoided.

7 Claims, 2 Drawing Sheets

ANTERIOR COMMISSURE LARYNGOSCOPE

BRIEF SUMMARY OF THE INVENTION

This invention relates to surgery, and particularly to improvements in laryngoscopes.

A laryngoscope is an endoscopic instrument used in the visualization of the interior of the larynx in diagnostic, therapeutic and surgical procedures. Although the instruments take various forms, the typical instrument comprises a metal tube approximately 17 cm. in length, with an L-shaped handle at one end by which the tube is manipulated by the surgeon. A typical instrument also has; one or more channels, extending along the sides of the tube, for receiving removable fiber optic light guides used to illuminate the portion of the larynx being examined through the instrument. The larynx can be observed through the laryngoscope with the aid of an operating microscope, and various specially adapted instruments, such as laryngoscopic forceps and scissors, can be used to carry out biopsies and other surgical procedures through the laryngoscope.

During laryngoscopy, the patient is normally supine, with the head tilted backward so that the mouth is aligned with the larynx. In use, therefore, the laryngoscope is situated with the axis of its tube generally horizontal.

The laryngoscope is typically used in conjunction with an operating microscope which is held by a suitable support at a distance from the proximal end of the tube to allow room for insertion of instruments through the tube. Although monocular operating microscopes have been used, binocular operating microscopes are available in many operating rooms, and are preferred because they provide the surgeon with a three-dimensional view of the surgical field. A typical binocular microscope is the "Zeiss operating microscope". The Zeiss microscope is used in conjunction with laryngoscopes of various kinds.

One well-known type of laryngoscope is known as the "Holinger anterior commissure laryngoscope". In this instrument, the superior surface of the tube rises obliquely at the distal end to provide maximum visibility of the anterior commissure of the vocal cords, where as much as 80% of the pathology of the vocal cords occurs. The distal end is also flared laterally. The proximal end of the tube drops obliquely for improved visibility of the anterior commissure. The mid-portion of the tube is narrow, both vertically and laterally, to reduce the likelihood of damage to the patient's teeth, and to permit maneuvering of the tube by the surgeon in order to observe various portions of the larynx. Maneuverability is important, because, in some patients, the teeth, specifically the maxillary incisors get in the way of the laryngoscope, preventing the proximal end of the tube from being moved down to enable Visualization of the anterior commissure. To accomplish this, therefore, the tube is moved to one side so that its mid-point is positioned between the patient's molars. The proximal end of the tube can then be pushed down so that the anterior commissure can be seen.

It is not possible to take advantage of the binocular vision capabilities of the Zeiss operating microscope with a Holinger anterior commissure laryngoscope. The reason is that the included angle between rays extending from a point on the object being viewed to the centers of the objective lenses of the microscope is too large. Because of the narrow width of the tube, both rays cannot simultaneously extend through the laryngoscope tube to the surgical field. Attempting to use a binocular microscope with the Holinger laryngoscope is .annoying, because one eye always sees objects external to the laryngoscope. Binocular vision is therefore impossible.

Another type of laryngoscope, known as the "Jako micro-laryngoscope" utilizes a tube which has a generally triangular cross-section and which is continuously tapered down from proximal to distal end. The tube of this laryngoscope is wide enough to be used with a Zeiss operating microscope, and permits binocular vision of the surgical field. However, because the tube has a continuous taper, its width at the midpoint is too large to permit good maneuverability.

Still another type of laryngoscope is known as the "Dedo-Pilling micro-laryngoscope". The proximal portion of the tube of this laryngoscope has a generally pentagonal cross-section, and the instrument is more maneuverable than the Jako microlaryngoscope. The tube has an upward flare at the distal end, but, like the tube of the Jako instrument, it is continuously tapered down from the proximal to the distal end. It can be used with a Zeiss operating microscope, and affords binocular vision, but requires careful adjustment of the relationship between the microscope and the laryngoscope to avoid the problem, associated with the Holinger instrument, in which one eye sees objects outside the tube.

The Jako and Dedo-Pilling laryngoscopes will not fit a substantial percentage of patients because of the patients' anatomy.

The principal object of this invention is to provide a laryngoscope which is usable with a binocular operating microscope, but which does not require careful adjustment of the microscope in order to prevent the surgeon from seeing objects outside the laryngoscope tube. It is also an object of the invention to provide a laryngoscope which can be used with a binocular operating microscope on a large percentage of patients.

The laryngoscope in accordance with the invention is designed for use with a binocular operating microscope having two objective lenses situated with their centers at a predetermined spacing, typically approximately 22 mm., with the lenses having centerlines converging on a point at a predetermined distance from the lenses, typically in the range of approximately 300 to 400 mm. The laryngoscope comprises a rigid, elongated, hollow tube having an interior wall and an axis of elongation and having openings at distal and proximal ends. When the tube is situated in a substantially horizontal condition, it has a top, a bottom and two sides. The top of the tube is flared at the distal end to provide for visibility of the anterior commissure. The sides of the tube are also flared at the .distal end. Furthermore, at least the two sides of the tube are also flared at the proximal end. The opening at the proximal end preferably has a maximum width, measured from side to side, of approximately 19 to 25 mm., so that the tube permits viewing, along either one of the centerlines, of any point on an area of the larynx located adjacent to the distal end of the tube having a width approximately equal to the width of the distal opening, while the other centerline intersects either said area of the larynx or said interior wall of the tube. The surgeon may not achieve true binocular vision through the laryngoscope at all times. However, the eye which is not viewing the larynx sees only the dark interior wall of the laryngoscope. Consequently, the surgeon is not annoyed by seeing the larynx with one eye and lighted objects outside the laryngoscope with the other eye.

Further objects, details and advantages of the invention will be apparent from the following detailed description, when read in conjunction with the drawings.

DETAILED DESCRIPTION

Figure 1:
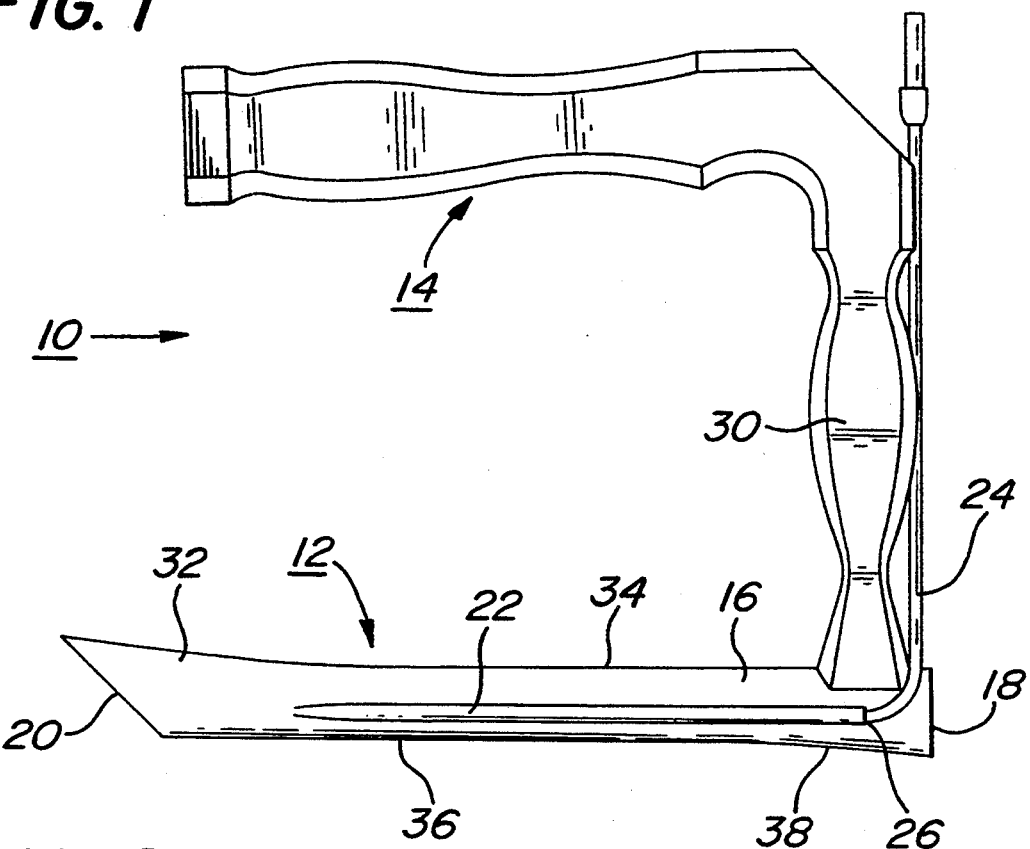
FIG. 1 is a side elevation of a laryngoscope in accordance with the invention.

As shown in FIG. 1, the laryngoscope 10 comprises an elongated, hollow tube 12 having an L-shaped handle 14 attached to its outer wall 16 near its proximal end 18. The tube has a bevelled opening at its distal end 20. A light guide channel 22 is formed along one side of the tube and has an opening (not shown) within the tube near the distal end. A fiberoptic light guide 24 extends through an opening at the proximal end 26 of the channel and through the channel so that it can illuminate the parts of the patient's anatomy being viewed through the tube. A vertical groove 28, formed in portion 30 of handle 14, supports the external portion of light guide 24.

A portion of the upper part of the tube, extending for approximately one-third the length of the tube from the distal tip, is flared upward at 32 to optimize visibility of the anterior commissure. The remaining two-thirds of the upper part of the tube, which is designated by numeral 34, is substantially straight.

The major part 36 of the bottom part of the tube is straight. However, the tube is flared downward at 38 near the proximal end, as in the case of the conventional Holinger laryngoscope, for improved visibility of the anterior commissure.

Figure 3:
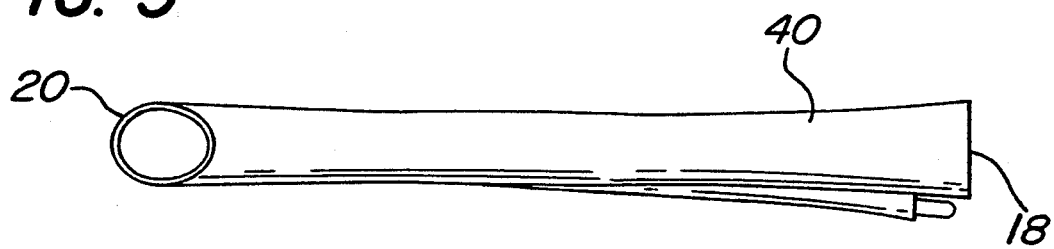
FIG. 3 is a bottom plan view thereof.

As shown in FIG. 3, the sides of the tube are flared outward at 40 toward the proximal end 18, through a distance extending approximately one-third the length of the tube and terminating at the proximal end. The sides of the tube are also flared slightly toward the distal end 20.

Figure 2:
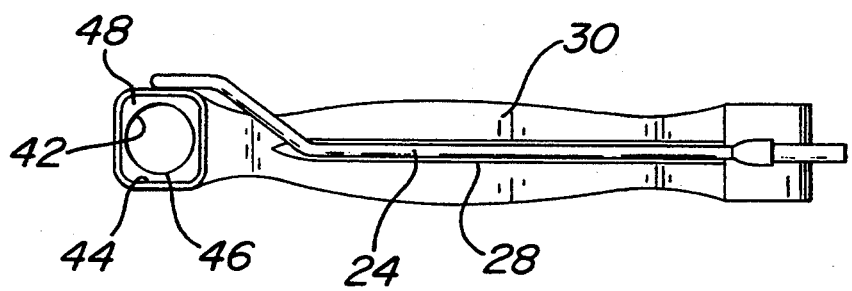
FIG. 2 is a rear elevational view thereof.

As shown in FIG. 2, the mid-portion 42 of the lumen of the tube is narrower than proximal opening 44. Proximal opening 44 is generally in the shape of a rectangle with rounded corners. Parts 46 and 48 of the interior wall of the flared portion 40 of the tube are shown in FIG. 2. These are the parts of the interior wall which are intersected by the centerlines of the binocular microscope lens which is not viewing the larynx through the laryngoscope tube.

The dimensions of the preferred laryngoscope tube are as follows:

Overall length (at top): 168 mm.
Length of bottom 149 mm.
Width of distal opening: 12 mm.
Narrowest width of lumen: 8.5 mm.
Length of straight part 34: 110 mm.
Length of straight part 36: 110 mm.
Length of flared part 40: 55 mm.
Width of proximal opening: 19 mm.
Height of proximal opening: 15.5 mm.
Diagonal of proximal opening: 20.5 mm.

In a Zeiss operating microscope, the centerlines of the objective lenses converge at a distance in the range of 300 to 400 mm. from the lenses, depending on which objective lenses are used. The angle of convergence ranges from 4.10° for the 300 mm. lenses to 3.15° for the 400 mm. lenses.

Figure 4:
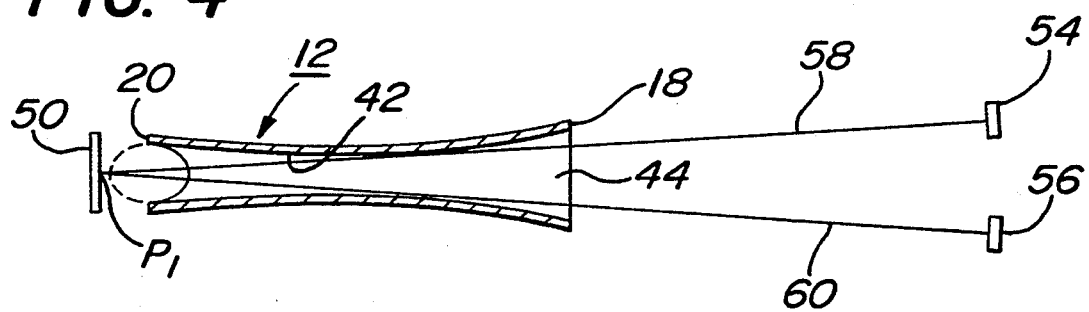
FIGS. 4, 5 and 6 are diagrammatic horizontal sections showing relationships between the laryngoscope of the invention and an operating microscope, and are exaggerated for the purpose of illustration.

FIG. 4 shows laryngoscope tube 12 with its distal end 20 located in proximity to a patient's vocal cords 50. The objective lenses 54 and 56 of a binocular operating microscope have their centerlines converging on a point $P_1$ on vocal cords 50. Point $P_1$ is aligned with the central axis of the tube, and both centerlines 58 and 60 extend through the narrow mid-portion 42 of the tube without intersecting the tube wall. Consequently it is possible to obtain a three-dimensional view of at least a centrally-located portion of the vocal cords.

Figure 5:
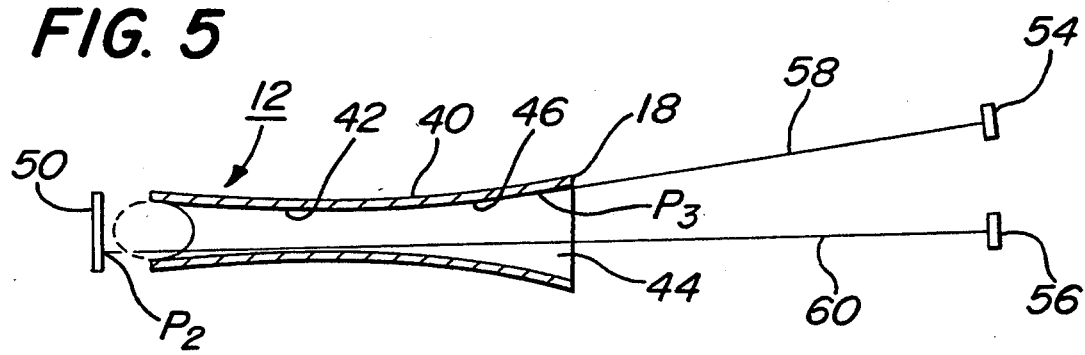
Figure 6:
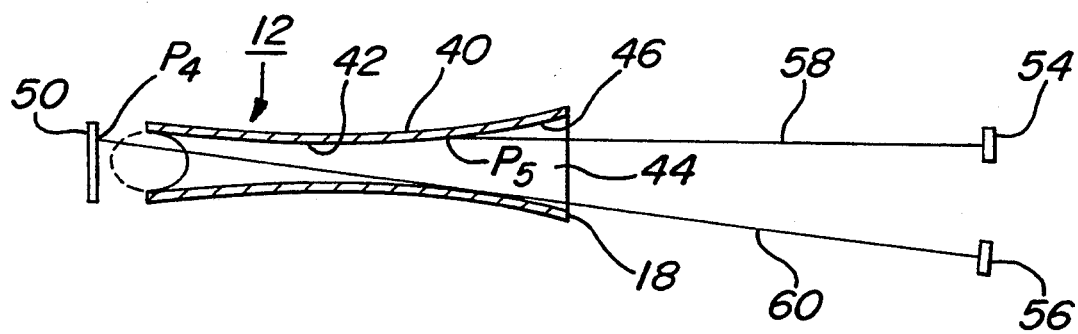

However, when attempting to view a point on the vocal cords off the axis of the laryngoscope by moving the operating microscope without moving the laryngoscope, the situation is as illustrated in FIG. 5 or FIG. 6. In FIG. 5, the microscope is moved toward the surgeon's right in order to view point $P_2$, which is to the left of the axis of the laryngoscope tube. In this case, the surgeon views point $P_2$ with the left eye through objective lens 56 along centerline 60. Because objective lens 58 is moved too far to the right, centerline 58 can no longer extend through the tube. However, because of the flaring of the proximal one-third of the tube at 40, centerline 58 intersects part 46 of the interior wall at point $P_3$, and does not extend past the tube on the outside. Consequently, the right eye of the surgeon sees only the relatively dark interior wall of the tube, while the right eye views the vocal cords in two dimensions.

FIG. 6 illustrates what occurs when the surgeon is viewing, again with the left eye, a point $P_4$ which is offset laterally to the right of the central axis of the tube. The microscope is moved to the surgeon's left in order to view point $P_4$ along centerline 60, which extends through the tube without intersecting its walls. Centerline 58, however, again intersects part 46 of the interior wall, this time at point $P_5$. Again, the right eye sees only the interior wall of the tube.

From FIGS. 4-6, it will be apparent that the surgeon is able to view almost the entire width of the vocal cord structure exposed by the laryngoscope without the annoyance of having one eye see objects external to the laryngoscope. Because the mid-portion of the tube is narrow, as in a conventional Holinger laryngoscope, the tube can be maneuvered from left to right, when necessary, in order to view the anterior commissure. Therefore, the laryngoscope is usable with patients whose anatomy does not permit use of the Jako and Dedo-Pilling laryngoscopes.

The laryngoscope described above is designed for use with a Zeiss operating microscope in which the centerlines of the objective lenses converge at a distance of 300 to 400 mm., depending on which of the available objective lenses are used. The laryngoscope may, of course, be modified to accommodate other operating microscopes and other objective lenses, by changing the amount of flare at the proximal end of the tube, as necessary. Various other modifications, which will occur to those skilled in the art may be made without departing from the scope of the invention as defined in the following claims.

I claim:

1. A laryngoscope for use with a binocular surgical microscope for viewing the anterior commissure of the vocal cords comprising:

a rigid, elongated, hollow tube having an interior wall and an axis of elongation and having openings at distal and proximal ends, the tube having a central portion located at an intermediate position between its distal and proximal ends, and, when situated with its axis in a substantially horizontal condition, having a top and a bottom and two sides;

the top of the tube being flared from said central portion toward the distal end to provide for visibility of the anterior commissure;

the sides of the tube also being flared from said central portion toward the distal end; and at least the two sides of the tube also being flared from said central portion toward the proximal end;

whereby the width of the tube at said central portion, measured from side to side is less than the widths of the tube at said distal and proximal ends, for improved maneuverability and compatibility with a wide range of patient anatomy.

2. A laryngoscope according to claim 1 in which the flare at the distal end extends approximately one-third the length of the tube.

3. A laryngoscope according to claim 1 in which the proximal opening has a maximum width, measured from side to side, of approximately 19 to 25 mm., whereby, when used with a binocular operating microscope having two objective lenses situated with their centers at a spacing of approximately 22 mm., said lenses having centerlines converging on a point at a distance of approximately 300 to 400 mm. from said lenses, the tube permits viewing, along one of said centerlines, of any point on an area of the larynx, located adjacent to the distal end of the tube, having a width approximately equal to the width of the distal opening, while the other centerline intersects either said area of the larynx or said interior wall of the tube.

4. A laryngoscope according to claim 3 in which the flare at the distal end extends approximately one-third the length of the tube.

5. A laryngoscope according to claim 4 in which the width of the lumen in the middle one-third of the length of the tube is approximately 8.5 mm.

6. In combination with a binocular operating microscope having two objective lenses situated with their centers at a predetermined spacing, said lenses having centerlines converging on a point at a predetermined distance from said lenses, a laryngoscope for viewing the anterior commissure of the vocal cords comprising:

a rigid, elongated, hollow tube having an axis of elongation and having distal and proximal ends, the tube having a central portion located at an intermediate position between its distal and proximal ends, and, when situated with its axis in a substantially horizontal condition, having a top and a bottom and two sides;

the top of the tube being flared from said central portion toward the distal end to provide for visibility of the anterior commissure;

the sides of the tube also being flared from said central portion toward the distal end; and at least the two sides of the tube also being flared from said central portion toward the proximal end, whereby the width of the tube at said central portion is less than the Widths of the tube at said distal and proximal ends, for improved maneuverability and compatibility with a wide range of patient anatomy;

said two sides of the tube terminating, at said proximal end, in an opening having a width, measured from side to side, such that the tube permits viewing, along one of said centerlines, of any point on an area of the larynx located adjacent the distal end of the tube, said area having a width approximately equal to the width of the distal opening, while the other centerline intersects either said area of the larynx or said interior wall of the tube.

7. In combination with a binocular operating microscope having two objective lenses situated with their centers at a spacing of approximately 22 min., said lenses having centerlines converging on a point at a distance of approximately 300 to 400 mm. from said lenses, a laryngoscope for viewing the anterior commissure of the vocal cords comprising:

a rigid, elongated, hollow tube having an axis of elongation and having distal and proximal ends, the tube having a central portion located at an intermediate position between its distal and proximal ends, and, when situated with its axis in a substantially horizontal condition, having a top and a bottom and two sides;

the top of the tube being flared from said central portion toward the distal end to provide for visibility of the anterior commissure;

the sides of the tube also being flared from said central portion toward the distal end; and at least the two sides of the tube also being flared from said central portion toward the proximal end, whereby the width of the tube at said central portion is less than the widths of the tube at said distal and proximal ends, for improved maneuverability and compatibility with a wide range of patient anatomy;

said two sides of the tube terminating, at said proximal end, in an opening having a maximum width, measured from side to side, of approximately 19 to 25 mm; whereby the tube permits viewing, along one of said centerlines, of any point on an area of the larynx, adjacent to the distal end of the tube, having a width approximately equal to the width of the distal opening, while the other centerline intersects either said area of the larynx or said interior wall of the tube.

* * * * *